US010088833B2

(12) United States Patent
MacLaverty (10) Patent No.: US 10,088,833 B2
(45) Date of Patent: Oct. 2, 2018

(54) PRINTING OF OBJECTS FOR MEDICAL USE (71) Applicant: Varian Medical Systems, Inc., Palo Alto, CA (US)

(72) Inventor: Ronan MacLaverty, Helsinki (IE)

(73) Assignee: Varian Medical Systems International AG., Cham (CH)

(*) Notice: Subject to any disclaimer, the term of this patent is extended or adjusted under 35 U.S.C. 154(b) by 628 days.

(21) Appl. No.: 14/502,624

(22) Filed: Sep. 30, 2014

(65) Prior Publication Data
US 2015/0094838 A1 Apr. 2, 2015

Related U.S. Application Data (60) Provisional application No. 61/884,328, filed on Sep. 30, 2013.

(51) Int. Cl.
G06F 19/00 (2018.01)
G05B 19/4099 (2006.01)
G06F 17/50 (2006.01)
B29C 64/386 (2017.01)
B33Y 50/02 (2015.01)

(52) U.S. Cl.
CPC ........ *G05B 19/4099* (2013.01); *B29C 64/386* (2017.08); *G06F 17/50* (2013.01); *B33Y 50/02* (2014.12); *Y02P 90/265* (2015.11)

(58) Field of Classification Search
CPC .................................................. G05B 19/4099
USPC .......................................................... 700/98
See application file for complete search history.

(56) References Cited

U.S. PATENT DOCUMENTS

| 9,449,383 | B2* | 9/2016 | Thomson | G06T 7/0012 |
| 2012/0253495 | A1* | 10/2012 | Wright | G06T 17/20 700/98 |
| 2013/0198463 | A1* | 8/2013 | Hintz | A61N 1/3787 711/154 |
| 2014/0276035 | A1* | 9/2014 | Jeraj | A61B 5/4848 600/431 |
| 2016/0256709 | A1* | 9/2016 | Robar | A61B 6/5217 |
| 2016/0271379 | A1* | 9/2016 | Pouliot | A61B 8/085 |

* cited by examiner

Primary Examiner — Evral E Bodden (57) ABSTRACT

An artifact for radiation therapy is produced by accessing image data comprising images including a target volume inside a patient. A design for the artifact is generated based on the image data. The design is customized to a radiation therapy treatment plan for the patient. A printing plan is generated based on the design. A three-dimensional printer is controlled using the printing plan to build an object that corresponds to the design.

19 Claims, 5 Drawing Sheets

PRINTING OF OBJECTS FOR MEDICAL USE

RELATED U.S. PATENT APPLICATION

This application claims priority to the U.S. Provisional Application filed on Sep. 30, 2013, entitled "3D Printing of Objects Used in Radiotherapy," Ser. No. 61/884,328, hereby incorporated by reference in its entirety.

BACKGROUND

The use of radiation therapy (radiotherapy) to treat cancer is well known. Typically, radiation therapy involves focusing a beam of radiation (e.g., proton, x-ray, or electron radiation) onto a target volume to diagnose an afflicted area or to monitor a tumor or lesion. A beam of high energy proton, x-ray, or electron radiation ("therapeutic radiation") is subsequently directed into the target volume during treatment.

A radiation therapy device typically includes a surface (e.g., a platform or couch) to support the patient and an overhead radiation source that emits the therapeutic radiation beam. The patient is positioned directly below the radiation source while in a supine position on the couch, and the radiation source directs the beam into the targeted volume (e.g., the tumor being treated). The radiation beam may be moved to "paint" the target volume, or the radiation beam may be shaped so that its cross-section approximates the shape of the target volume, so that the beam falls only on the target volume and not on surrounding, healthy tissue. The strength or intensity of the beam is selected depending on the thickness of the target volume and its depth within the patient, as well as other factors.

During treatment, it is important to keep the patient stationary (immobilized), so that the beam remains pointed at just the target volume, and/or so that the cross-section of the beam at the point where it intersects the target volume does not change. Otherwise, the radiation beam may not cover the entire target volume or might land on tissue outside the target volume.

Fixation or immobilization devices are used to secure a patient's position and keep the patient stationary during radiotherapy. Boluses or shields are used to shape or alter the radiation beam during treatment.

The standard treatment flow is to first scan and image the patient prior to treatment to detect internal organs and locate the target volume (e.g., the tumor). Fixation devices customized for the patient are designed and a treatment plan is generated. Boluses customized to the patient and treatment plan are designed. The designs for fixation devices and boluses (which may be referred to collectively as artifacts) are sent to a manufacturer. The manufactured artifacts are delivered to the treatment center, where they are tested prior to beginning radiotherapy. If changes are needed, the process of interacting with the manufacturer is repeated. The patient then returns and treatment can begin.

The conventional approach described above is problematic for a variety of reasons. First, multiple patient visits are required—at least one visit is required prior to treatment in order to design the artifacts. Also, the need to hire a manufacturer increases costs. Furthermore, time is lost while artifacts are shipped from and perhaps back to the manufacturer.

SUMMARY

In embodiments according to the present invention, artifacts such as but not limited to fixation devices and boluses are generated using three-dimensional (3D) printing techniques. As noted above, a patient is scanned and imaged to create a 3D model of internal organs and the target volume. The 3D model can be translated into files that can be used by a 3D printer to manufacture artifacts. Alternatively, a 3D printer can be used to create molds that in turn can be used to manufacture artifacts.

In an embodiment, an artifact for radiation therapy (radiotherapy) is produced by accessing image data comprising images including a target volume inside a patient. A design for the artifact is generated based on the image data. The design is customized to a radiotherapy treatment plan for the patient. A printing plan is generated based on the design. A 3D printer is controlled using the printing plan to build an object that corresponds to the design.

Consequently, artifacts can be fabricated and a patient can be treated in the same visit. Because the artifacts can be fabricated on-site without involving an outside manufacturer, costs are reduced and time is saved. Artifacts can be tested on the patient and modified as needed without delay. The artifacts may be fabricated using less expensive materials, and may also be recycled. Because the artifacts can be fabricated as needed, there is no need to store them between treatments or over the longer term.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "generating," "accessing," "controlling," "translating," "transforming," "executing," "outputting", or the like, refer to actions and processes (e.g., the flowchart 500 of FIG. 5) of a computing system or similar electronic computing device or processor (e.g., the computing system 600 of FIG. 6). The computing system or similar electronic computing device manipulates and transforms data represented as physical (electronic) quantities within the computing system memories, registers or other such information storage, transmission or display devices.

Portions of the detailed description that follows are presented and discussed in terms of a method. Although steps and sequencing thereof are disclosed in figures herein (e.g., FIGS. 2 and 5) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

Figure 1:
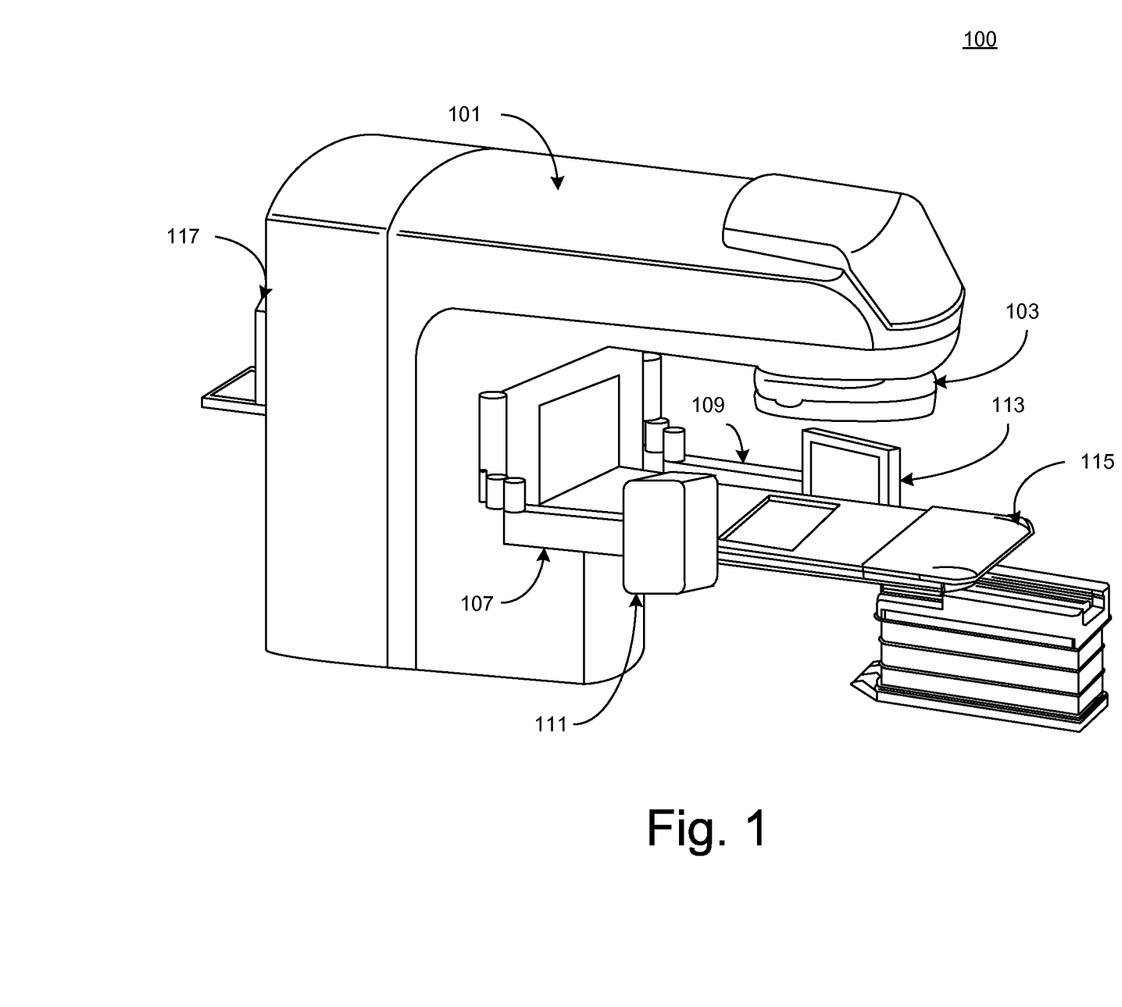
FIG. 1 is an example of a radiotherapy device with which embodiments according to the present invention can be used.

With reference now to FIG. 1, an illustration of an example of a radiation therapy device 100 is depicted, in accordance with one embodiment of the present invention. In one configuration, the radiation therapy device 100 includes a support structure (e.g., a gantry 101), a therapeutic radiation source 103, a number of robotic arms (e.g., robotic arms 107 and 109), a diagnostic radiation source 111, a diagnostic radiation imager 113, and a patient couch 115. In some embodiments, the radiation therapy device 100 may include a control subsystem 117 that includes a communicatively coupled computing device having a processor and a memory.

In one embodiment, the end of the gantry 101, positioned above the patient couch 115, is attached to a therapeutic radiation source 103. The robotic arms 107 and 109 are mounted on the gantry 101. In some embodiments, the robotic arms 107 and 109 may be extendable and retractable. In some embodiments, the robotic arms 107 and 109 are independent from each other and opposable. In one embodiment, a diagnostic radiation source 111 is coupled to the end of a robotic arm (e.g., the robotic arm 107) extending towards patient couch 115. In further embodiments, a diagnostic radiation imager 113 is coupled to the end of an alternate robotic arm (e.g., robotic arm 109), also extending towards patient couch 115. The robotic arms 107 and 109 are capable of maneuvering to allow for positioning of the diagnostic radiation source 111 and the diagnostic radiation imager 113 to any position in space within the travel range of the robotic arm; each of the robotic arms 107 and 109 is capable of pivoting at different pivot points and along a number of independent axes. In still further embodiments, the gantry 101 is also rotatable along one or more axes, allowing for even greater travel ranges for the plurality of robotic arms 107 and 109 and for movement of the therapeutic radiation source 103.

While receiving treatment, a patient is positioned (typically supine) on patient couch 115. A target volume (generally disposed within or about the patient subject) is acquired. According to one embodiment, the target volume is acquired by generating a volumetric image of the area within the patient. A volumetric image of the area is acquired by, for example, generating a three dimensional image using diagnostic radiation source 111 in conjunction with diagnostic radiation imager 113. In one embodiment, diagnostic radiation source 111 may comprise, for example, an x-ray radiation source. The robotic arm 107 attached to diagnostic radiation source 111 can be positioned about the target volume for computer tomography images using a cone x-ray beam to acquire volumetric information. Positioning of the robotic arm 107 may be performed by movement of the robotic arm 107 which may include, but is not limited to, rotating, swiveling, extending and retracting the robotic arm.

In one embodiment, diagnostic radiation source 111 and diagnostic radiation imager 113 may be positioned around a target volume such that the target volume is between the diagnostic radiation source 111 and diagnostic radiation imager 113 while volumetric imaging is being acquired. The radiation (e.g., x-rays) emitted by the diagnostic radiation source 111 travel through the target subject, are received by the diagnostic radiation imager 113 and an image of the target subject is thus generated, in accordance with conventional techniques. The imaging generated from the diagnostic radiation process is subsequently utilized to provide targeting information which can be used to accurately direct the therapeutic radiation from therapeutic radiation source 103 to the target volume from various angles.

In one embodiment, the diagnostic radiation imager 113 can be attached to a second robotic arm 109 opposite from the robotic arm 107 attached to diagnostic radiation source 111. In further embodiments, the robotic arm 109, though still independent of, attached to the diagnostic radiation imager 113 is positioned in concert with the robotic arm 107, such that the diagnostic radiation imager 113 is in constant alignment to diagnostic radiation source 111 and on a side opposite diagnostic radiation source 111 with respect to the target volume.

Once aligned, diagnostic radiation (e.g., an x-ray beam) from the diagnostic radiation source 111 is propagated toward the target volume that is situated on or about the patient couch 115. The diagnostic radiation passes through the target volume and is received by the diagnostic radiation imager 113. The resulting image(s) generated by the diagnostic radiation imager 113 may then be used to reposition the patient using the patient couch 115 to achieve a greater degree of accurate targeting. The therapeutic radiation source 103 subsequently propagates the therapeutic radiation into the target volume within the repositioned patient.

The control subsystem (computing device) 117 may be mounted on the gantry 101, or may be coupled to the radiation therapy device 100, via one or more data transport cables. In further embodiments, control subsystem (computing device) 117 may communicate remotely with the radiation therapy device 100. Once initiated, an imaging acquisition process may position the robotic arms 107 and 109 coupled to the diagnostic radiation source 111 and diagnostic radiation imager 113 to acquire a volumetric image.

As discussed above, a volumetric image may be constructed from images acquired by positioning the diagnostic radiation source 111 and diagnostic radiation imager 113. Once a volumetric image has been constructed for a target volume, the target volume may be repositioned (e.g., by repositioning the patient) to receive therapeutic radiation from the therapeutic radiation source 103 such that the therapeutic radiation may be directed into the target volume with greater precision with respect to the original (or former) position of the target volume (patient). In one embodiment, the therapeutic radiation source 103 can be repositioned relative to the target volume by moving the gantry 101.

Figure 2:
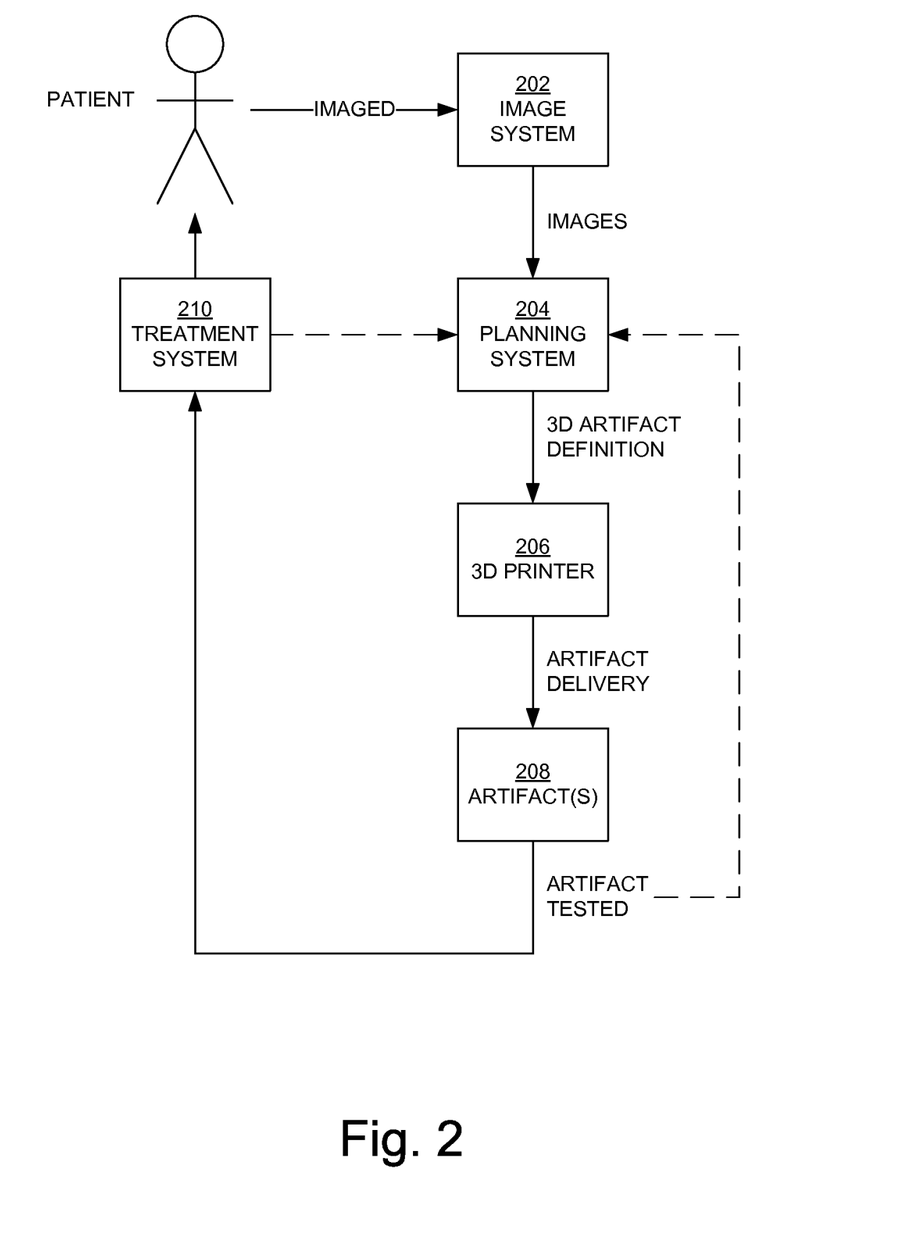
FIG. 2 is a block diagram illustrating components in a process for creating artifacts in an embodiment according to the present invention.

FIG. 2 is a block diagram illustrating components in a process for creating artifacts, such as but not limited to fixation devices, boluses, blocks, and shields, in an embodiment according to the present invention. Examples of artifacts are presented in FIGS. 3 and 4, below.

In the example of FIG. 2, the patient is imaged using an image system 202, such as x-ray, magnetic resonance imaging (MRI), computed tomography (CT), and others. When CT or MRI imagery, for example, is used, a series of two-dimensional images are taken from a three-dimensional volume. Each two-dimensional image is an image of a cross-sectional "slice" of the three-dimensional volume. The resulting collection of two-dimensional cross-sectional slices can be combined to create a three-dimensional model or reconstruction of the patient's anatomy (e.g., internal organs). The three-dimensional model or three-dimensional reconstruction will contain organs of interest, which may be referred to as structures of interest. Those organs of interest include the organ targeted for radiation therapy (a target volume), as well as other organs that may be at risk of radiation therapy exposure. The portion of the three-dimensional model or reconstruction that contains the organs of interest may be referred to as a target volume.

Structure(s) of interest can be viewed by combining the series of two-dimensional cross-sectional slices into a single three-dimensional image where the structure(s) of interest may be displayed as solid, opaque, translucent, etc., objects that may then be manipulated (e.g., rotated) to allow viewing from multiple angles.

One purpose of the three-dimensional model of the structure(s) of interest is the preparation of a radiation therapy treatment plan. Radiation therapy treatment plans are used during medical procedures to selectively expose precise areas of the body, such as cancerous tumors, to specific doses of radiation to destroy the undesirable tissues. To develop a patient-specific radiation therapy treatment plan, information is extracted from the three-dimensional model to determine parameters such as organ shape, organ volume, tumor shape, tumor location in the organ, and the position or orientation of several other structures of interest as they relate to the affected organ and any tumor. The radiation therapy treatment plan can specify, for example, how many radiation beams to use, which angle each of the beams will be delivered from, and whether attenuating artifacts (e.g., boluses and shields) are to be used.

In embodiments according to the present invention, the images from the image system 202 are input to a planning system 204. The planning system 204 can be implemented using a computing system. The planning system 204 broadly represents any single or multi-processor computing device or system capable of executing computer-readable instructions. Examples of a planning system 204 include, without limitation, workstations, laptops, client-side terminals, servers, distributed computing systems, handheld devices, or any other computing system or device. In its most basic configuration, the planning system 204 may include at least one processor and a system memory. The planning system 204 may also include a display and a user-input device (e.g., a mouse and keyboard). Additional information is provided in conjunction with FIG. 6, below.

Continuing with reference to FIG. 2, the planning system 204 executes software that is capable of producing printing plans for artifacts customized to the patient and to the treatment plan devised for the patient. The software may itself translate the output of the image system 202 (e.g., the three-dimensional model) into files that can be used by the 3D printer 206. For example, the software may access the DICOM (Digital Imaging and Communications in Medicine) plan and image files and produce files that can be used by the 3D printer 206. Alternatively, software may be used by a designer to produce such files based on the output of the image system 202 and also based on the treatment plan. The printing plans may be a design for an artifact itself, or it may be a design for a mold that can be used to fabricate the artifact. The planning system 204 outputs the files to the 3D printer 206, which produces the artifacts and/or molds.

3D printing is also referred to as additive manufacturing. Generally speaking, 3D printing refers to a process of manufacturing an object (e.g., an artifact or mold) by laying down successive layers of material, each layer having its own shape, from bottom to top, thereby forming the object.

An artifact 208 can be produced by the 3D printer 206 using a range of different materials suitable for such devices; that is, using materials that have the necessary radiological properties. If the 3D printer 206 is not capable of using such materials, then it can instead produce a mold that can be used to produce an artifact made of suitable materials. An artifact can be 3D-printed as a single piece, or it can be 3D-printed as multiple pieces that are subsequently assembled. Also, a relatively generic version of an artifact can be fabricated in bulk ahead of time, and customized pieces can subsequently be 3D-printed and attached to the generic version to create a customized artifact. The generic version may itself be fabricated using the 3D printer.

Each artifact 208 can be tested for fit and function; for example, its design can be modified as needed (e.g., using the planning system 204), the modified design can be submitted to the 3D printer 206, and a new version of the artifact 208 can be produced. Once the artifact(s) needed for radiotherapy are ready, they can be used with the treatment system 210 (e.g., the radiation therapy device 100 of FIG. 1) to treat the patient according to the treatment plan. As radiotherapy is performed, new or modified artifacts can be produced depending on how the treatment progresses.

Figure 3:
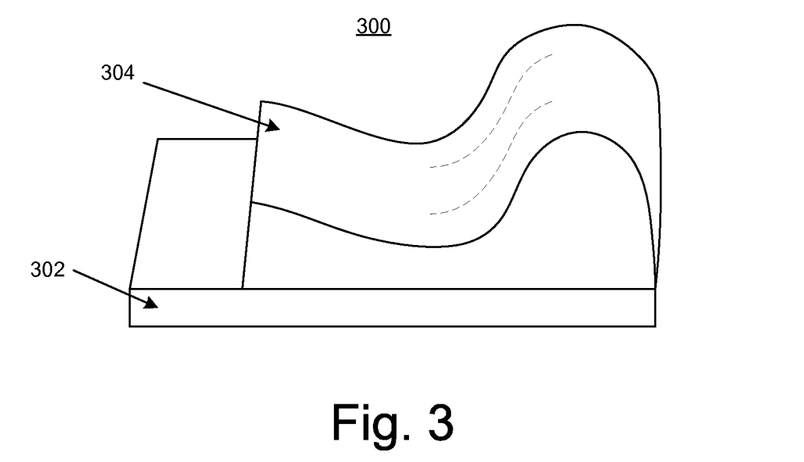
FIG. 3 is an example of an artifact that can be 3D-printed in embodiments according to the present invention.

FIG. 3 is an example of an artifact 300 that can be 3D-printed in embodiments according to the present invention. The artifact 300 may be used as a headrest, for example. In this example, the artifact 300 includes a base plate 302 and a support 304. In an embodiment, the base plate 302 and support 304 can be 3D-printed as a single piece. In other words, for example, the 3D printer fabricates the base plate 302 portion first, and then transitions directly into fabrication of the support 304 portion.

In another embodiment, the artifact 300 can be 3D-printed as multiple pieces that are then assembled to form the completed artifact. For example, the base plate 302 can be 3D-printed as one piece and the support 304 can be fabricated as a second piece, and then the two pieces can be attached to one another.

In yet another embodiment, part of the artifact 300 can be prefabricated, and then one or more other 3D-printed parts can be attached to the prefabricated part to form the completed artifact. Thus, one part (the prefabricated part) of the artifact can be generic or standardized, and one or more other parts can be 3D-printed and then attached to the prefabricated part to form an artifact that is specific to the patient and/or radiation therapy treatment plan. For example, the base plate 302 may be mass-produced, and a customized version of the support 304 can be 3D-printed and then attached to the base plate.

Alternatively, a mold corresponding to the shape of the artifact 300 can be 3-D printed. In an embodiment, a single mold can be 3D-printed, corresponding to the entire shape of the artifact 300 (e.g., the mold is for both the base plate 302 and the support 304). In another embodiment, a mold can be produced for each part of the artifact or for some combinations of its parts.

The artifact 300 can be custom-designed for the patient when the patient arrives for treatment. Thus, a visit prior to treatment is not required in order to design the artifact. The artifact 300 can be discarded or recycled after use, so it is not necessary to take up space to store it; instead, a new version of the artifact can be 3D-printed.

Figure 4:
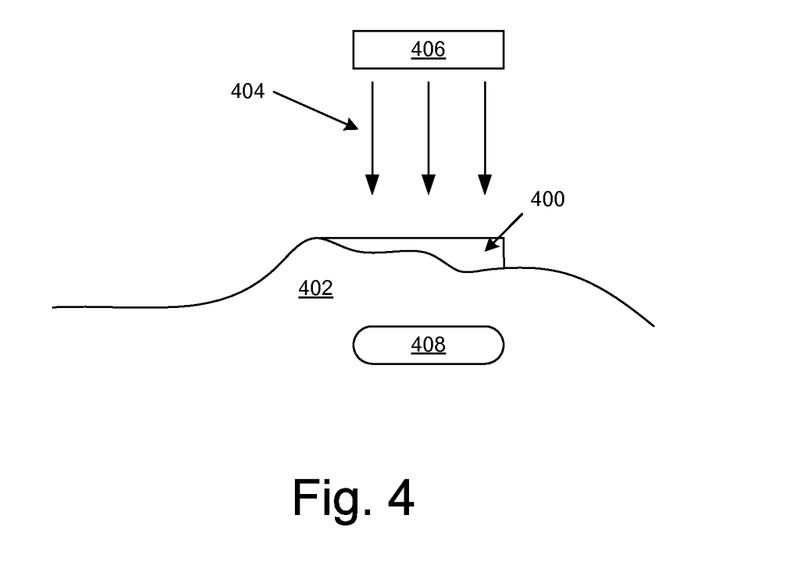
FIG. 4 is another example of an artifact that can be 3D-printed in embodiments according to the present invention.

FIG. 4 is another example of an artifact 400 (e.g., a bolus) that can be 3D-printed in embodiments according to the present invention. Alternatively, a mold corresponding to the shape of the artifact 400 can be 3D-printed.

The artifact 400 has the same advantages described above. Namely, the artifact 400 can be custom-designed to fit the contours of the patient's body 402, for example, when the patient arrives for treatment. Thus, a visit prior to treatment is not required in order to design the artifact. The artifact 400 can be discarded or recycled after use, so it is not necessary to take up space to store it; instead, a new version of the artifact can be 3D-printed. Also, if the contours of the patient's body, for example, changes between visits, a new artifact can be 3D-printed to account for the changes. For example, the purpose of the artifact 400 (bolus) may be to ensure that any path of a radiation beam 404 from a source 406 to a target volume 408 will travel through substantially the same effective thickness of matter (body and bolus), so that the strength of the beam is roughly uniform across the entire target volume. Accordingly, any change in the contours of the patient's body can be quickly accounted for to accomplish that purpose.

Figure 5:
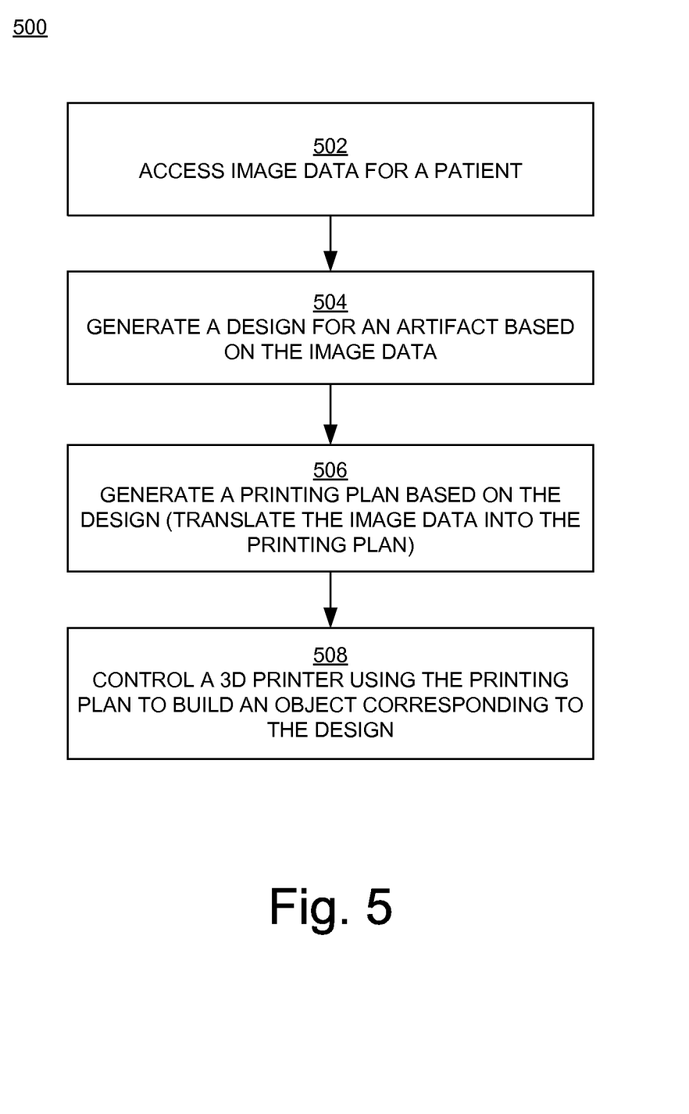
FIG. 5 is a flowchart of an example of a computer-implemented method for 3D-printing an artifact in an embodiment according to the present invention.

FIG. 5 is a flowchart 500 of an example of a computer-implemented method for 3D-printing an artifact in an embodiment according to the present invention. The flowchart 500 can be implemented as computer-executable instructions residing on some form of computer-readable storage medium (e.g., using computing system 600 of FIG. 6).

In block 502 of FIG. 5, image data including an image of a target volume inside a patient are accessed.

In block 504, a design for the artifact is generated based on the image data. The design of the artifact is specific to a radiation therapy treatment plan for the patient.

In block 506, a printing plan based on the design is generated. In an embodiment, the image data is translated into the printing plan.

In block 508, a 3D printer is controlled using the printing plan to build an object that corresponds to the design. In an embodiment, the object is the artifact itself, or a piece of the artifact. In another embodiment, the object is a mold that is complementary to the shape of the artifact, or complementary to the shape of a piece of the artifact.

Figure 6:
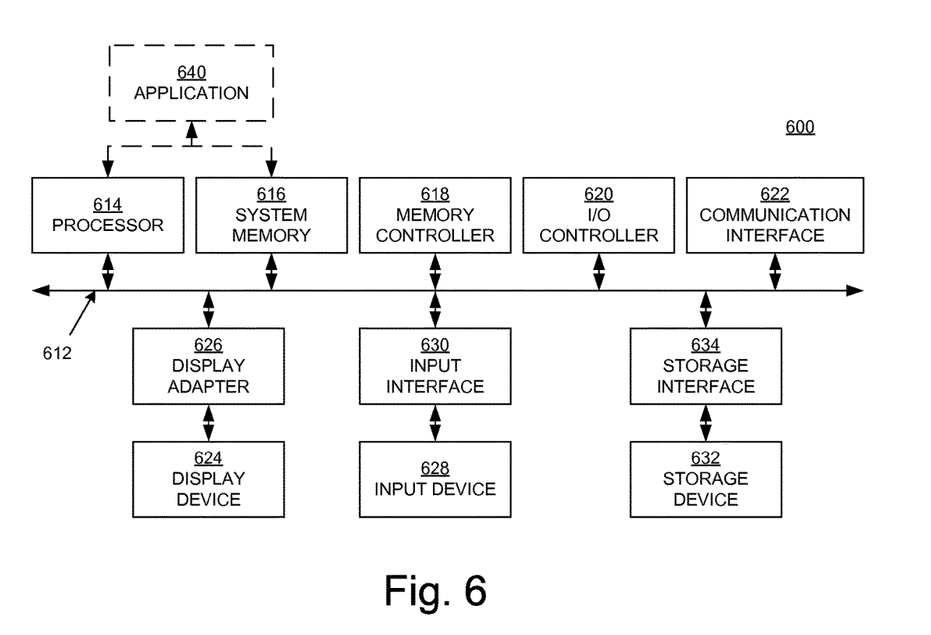
FIG. 6 is a block diagram of an example of a computing system capable of implementing embodiments according to the present invention.

FIG. 6 is a block diagram of an example of a computing system 600 capable of implementing embodiments of the present invention. In its most basic configuration, the computing system 600 may include at least one processor 614 and a system memory 616.

The processor 614 generally represents any type or form of processing unit capable of processing data or interpreting and executing instructions. In certain embodiments, the processor 614 may receive instructions from a software application or module. These instructions may cause the processor 614 to perform the functions of one or more of the example embodiments described and/or illustrated herein.

The system memory 616 generally represents any type or form of volatile or non-volatile storage device or medium capable of storing data and/or other computer-readable instructions.

The computing system 600 may also include one or more components or elements in addition to the processor 614 and the system memory 616. For example, in the example of FIG. 6, the computing system 610 includes a memory controller 618, an input/output (I/O) controller 620, and a communication interface 622, each of which may be interconnected via a communication infrastructure 612. The communication infrastructure 612 generally represents any type or form of infrastructure capable of facilitating communication between one or more components of a computing device.

The memory controller 618 generally represents any type or form of device capable of handling memory or data or controlling communication between one or more components of the computing system 600. The I/O controller 620 generally represents any type or form of module capable of coordinating and/or controlling the input and output functions of a computing device. The communication interface 622 broadly represents any type or form of communication device or adapter capable of facilitating communication between the example computing system 600 and one or more additional devices. The communication interface 622 may also allow the computing system 610 to engage in distributed or remote computing.

The computing system 600 may also include at least one display device 624 coupled to the communication infrastructure 612 via a display adapter 626. The computing system 600 may also include at least one input device 628 coupled to the communication infrastructure 612 via an input interface 630. Examples of the input device 628 include, without limitation, a keyboard or a pointing device.

The computing system 600 may also include a storage device 632. For example, the storage device 632 may be a magnetic disk drive (e.g., a so-called hard drive), a floppy disk drive, a magnetic tape drive, an optical disk drive, a flash drive, or the like.

The computing system 600 can execute an application 640 that allows it to perform operations (e.g., the operations of FIG. 5). A computer program containing the application 640 may be loaded into the computing system 600. For example, all or a portion of the computer program stored on a computer-readable medium may be stored in the memory 616. When executed by the processor 614, the computer program can cause the processor to perform and/or be a means for performing the functions of the example embodiments described and/or illustrated herein. Additionally or alternatively, the example embodiments described and/or illustrated herein may be implemented in firmware and/or hardware.

In summary, embodiments according to the present invention pertain to systems, software, and processes that can be used to 3D-print artifacts that are used in radiation therapy. Patient-specific devices can be readily, quickly, inexpensively, and effectively produced on-site (e.g., at a hospital or clinic) without an external manufacturer. The number of patient visits can be reduced. Artifacts can be quickly modified on-site after testing for fit and/or function or while the radiation therapy is being performed. Artifacts can be recycled and do not need to be stored.

Artifacts produced as described herein can be used in other ways including, for example, in surgical operations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method of producing an artifact for radiation therapy, the method comprising:
accessing image data stored in memory of the computer, the image data comprising images including an image of a target volume inside the patient;
generating a design for the artifact based on the image data, the design of the artifact specific to a radiation therapy treatment plan for the patient, the radiation therapy treatment plan comprising information that identifies a radiation dose to be delivered to the target volume and an angle between the target volume and an incident radiation beam;
translating, with software executing on the computer, the image data into a printing plan based on the design, wherein the printing plan comprises files that can be used with a three-dimensional printer;
controlling the three-dimensional printer using the files to build an object that corresponds to the design;
using the object during the radiation therapy; and
as the radiation therapy is being performed:
acquiring additional image data with a diagnostic radiation imager of the radiation therapy device;
generating a design for a second object based on the additional image data; and
three-dimensional printing the second object for use during the radiation therapy.

2. The method of claim 1, wherein the object is the artifact, wherein said controlling comprises controlling the three-dimensional printer using the printing plan to fabricate the artifact.

3. The method of claim 2, wherein the artifact is fabricated as a single piece.

4. The method of claim 2, wherein the artifact is fabricated as multiple pieces that comprise respective parts of the artifact and that fit together to produce the artifact.

5. The method of claim 1, wherein the object is a part of the artifact that is attached to a prefabricated part to produce the artifact.

6. The method of claim 1, wherein the object is a mold that is complementary to the shape of the artifact, wherein further said controlling comprises controlling the three-dimensional printer using the printing plan to fabricate the mold, wherein the artifact is subsequently produced using the mold.

7. The method of claim 1, wherein the artifact is selected from the group consisting of: a fixation device; a bolus; a block; a wedge; and a shield.

8. The method of claim 1, wherein the design is also specific to the patient.

9. A computing system comprising:
a central processing unit (CPU); and
memory coupled to the CPU and having stored therein instructions that, when executed by the computing system, cause the computing system to execute operations comprising:
accessing image data stored in a memory of the computing system, the image data comprising images of a patient's internal organs including an image of a target volume inside the patient;
executing software that translates the image data into a design for an artifact to be used during radiation therapy of the patient and that is customized to the patient and to a radiation therapy treatment plan for the patient and that translates the image data into a printing plan based on the design, wherein the printing plan comprises files that can be used with a three-dimensional printer;

outputting the files to the three-dimensional printer that executes the files to build an object that corresponds to the design;

using the object during the radiation therapy; and while the radiation therapy is being performed with a radiation therapy device: acquiring additional image data with a diagnostic radiation imager of the radiation therapy device, generating a design for a new object based on the additional image data, and three-dimensional printing the new object for use during the radiation therapy.

10. The computing system of claim 9, wherein the object is the artifact.

11. The computing system of claim 10, wherein the artifact is fabricated as a single piece.

12. The computing system of claim 10, wherein the artifact is fabricated as multiple pieces that comprise respective parts of the artifact and that fit together to produce the artifact.

13. The computing system of claim 9, wherein the object is a part of the artifact that is attached to a prefabricated part to produce the artifact.

14. The computing system of claim 9, wherein the object is a mold that is complementary to the shape of the artifact, wherein the artifact is subsequently produced using the mold.

15. The computing system of claim 9, wherein the artifact is selected from the group consisting of: a fixation device; a bolus; a block; a wedge; and a shield.

16. A non-transitory computer-readable storage medium having computer-executable instructions for causing a computing system to perform a method comprising:

transforming an image of a target volume inside the patient into a design for an artifact to be used during radiation therapy of the patient and that is customized to the patient and to a radiation therapy treatment plan for the patient;

generating additional computer-executable instructions based on the design and comprising files that can be used with a three-dimensional printer;

controlling the three-dimensional printer with the computer-executable instructions in the files, the three-dimensional printer additively manufacturing an object that corresponds to the design, wherein the object is used during the radiation therapy; and while the radiation therapy is being performed with a radiation therapy device: acquiring additional image data with a diagnostic radiation imager of the radiation therapy device, generating a design for a new object based on the additional image data, and three-dimensional printing the new object for use during the radiation therapy.

17. The non-transitory computer-readable storage medium of claim 16, wherein the object is selected from the group consisting of: the artifact, fabricated as a single piece; and the artifact, fabricated as multiple pieces that comprise respective parts of the artifact and that fit together to produce the artifact.

18. The non-transitory computer-readable storage medium of claim 16, wherein the object is a part of the artifact that is attached to a prefabricated part to produce the artifact.

19. The non-transitory computer-readable storage medium of claim 16, wherein the object is a mold that is complementary to the shape of the artifact, wherein the artifact is subsequently produced using the mold.

* * * * *